United States Patent [19]

Watanabe et al.

[11] 4,331,803

[45] May 25, 1982

[54] NOVEL ERYTHROMYCIN COMPOUNDS

[75] Inventors: Yoshiaki Watanabe, Tokyo; Shigeo Morimoto; Sadafumi Omura, both of Saitama, all of Japan

[73] Assignee: Taisho Pharmaceutical Co., Ltd., Japan

[21] Appl. No.: 266,060

[22] Filed: May 19, 1981

[30] Foreign Application Priority Data

Jun. 4, 1980 [JP] Japan ................... 55-75258
Nov. 12, 1980 [JP] Japan ................... 55-159128

[51] Int. Cl.³ .................. C07H 17/08; A01N 9/00
[52] U.S. Cl. ............................... 536/7.2; 424/180
[58] Field of Search ............. 536/9, 17 R; 424/180

[56] References Cited

U.S. PATENT DOCUMENTS 2,653,899  9/1953  Bunch et al. .................... 536/9
3,674,773  7/1972  Kurath ............................ 536/9
3,923,784 12/1975  Kierstad et al. ............... 536/9

Primary Examiner—Blondel Hazel
Attorney, Agent, or Firm—Wenderoth, Lind & Ponack

[57] ABSTRACT

Novel erythromycin compounds of the formula

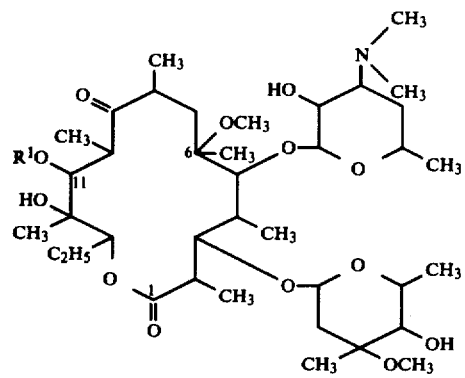

wherein $R^1$ is hydrogen or methyl, and a pharmaceutically acceptable salt thereof are disclosed. They exhibit excellent antibacterial activity against Gram-positive bacteria, acid stability and in vivo activity.

3 Claims, No Drawings

NOVEL ERYTHROMYCIN COMPOUNDS

The present invention relates to novel and useful erythromycin compounds of the formula

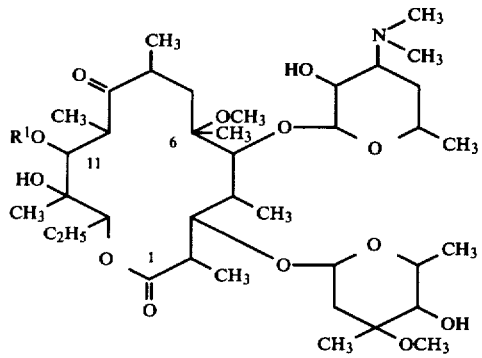

wherein $R^1$ is hydrogen or methyl, and a pharmaceutically acceptable salt thereof, having a strong antibacterial activity against Gram-positive bacteria.

The present invention is based on the discovery that novel compounds of formula(I) exhibit significantly antibacterial activity against Gram-positive bacteria even when administered orally, contrary to other closely analogous compounds such as erythromycin A. That is, although erythromycin A is known to be a useful macrolide antibiotic having a strong activity against Gram-positive bacteria, this compound has an undesirable property that it loses rapidly the antibacterial activity by the acid in stomach when administered orally, whereupon its blood concentration remains at a low level.

Accordingly, it is an object of the present invention to provide novel compounds of formula(I) valuable as medicines possessing not only excellent antibacterial activity against Gram-positive bacteria and acid stability but also remarkable in vivo activity.

The compound of formula(I) may be prepared, for example, by the following processes.

Namely, a compound of the formula

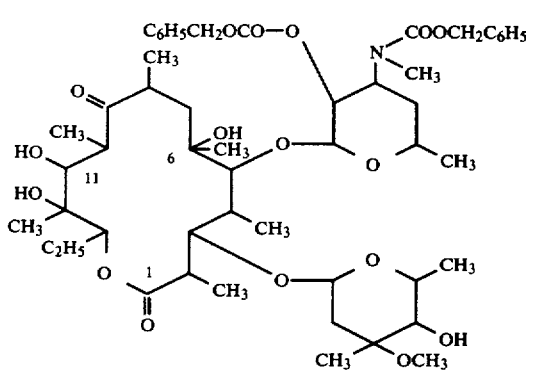

may be reacted with methyl iodide in the presence of a suitable base in a solvent to give a compound of the formula

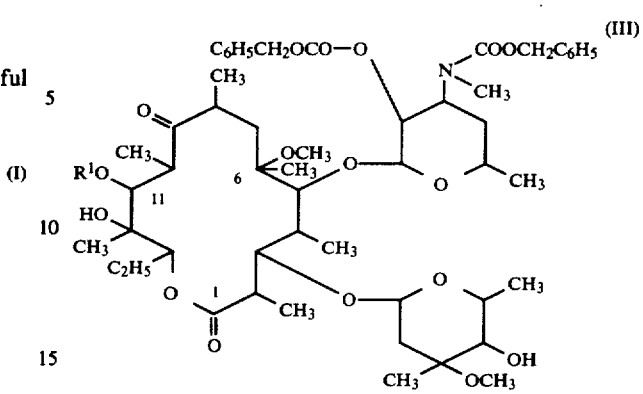

wherein $R^1$ is as defined above.

In the reaction, 5–10 moles of methyl iodide and 1–2 moles of the base are employed per mole of the compound of formula(II). The reaction proceeds at temperature ranging from −78° C. to room temperature, preferably from −15° C. to 5° C.

Examples of the base are an alkali metal hydride (e.g., lithium hydride, sodium hydride or potassium hydride), an alkali metal amide (e.g., lithium amide, sodium amide or potassium amide), butyllithium or lithium diisopropylamide.

Suitable solvents include polar aprotic solvents such as N,N-dimethylformamide, N,N-dimethylacetamide, dimethylsulfoxide or hexamethylphosphoric triamide, preferably N,N-dimethylformamide, dimethylsulfoxide or their mixture with tetrahydrofuran.

Purification of the compound of formula(III) may be carried out by using conventional methods such as silica gel column chromatography.

According to the method of E. H. Flynn et al. in Journal of the American Chemical Society, 77, 3104 (1955), the compound of formula(III) may be treated to remove benzyloxycarbonyl group by hydrogenolysis, and then subjected to the reductive methylation in the presence of excess amount of formaldehyde to give the compound of formula(I).

Alternatively, the compound of formula(I) may be obtained by performing removal of benzyloxycarbonyl group and N-methylation of the compound of formula(III), at the same time.

The pharmaceutically acceptable salts of the compounds of formula(I) include salts with organic acids such as an organic carboxylic acid (e.g., tartaric acid, citric acid, stearic acid or succinic acid), methanesulfonic acid, aminoethanesulfonic acid, an amino acid (e.g., aspartic acid or glutamic acid) or the like. These salts may be obtained by treating the compound of formula(I) with the corresponding acid by the conventional manners.

The compound of formula(II) may be prepared according to the above-described method of E. H. Flynn et al.

The compound of the present invention can be used as therapeutic agents against Gram-positive bacteria, mycoplasma and chlamydia in mammals. For these purposes, a compound of formula(I) may be administered orally or parenterally in a conventional dosage form such as tablet, capsule, powder, troches, dry mixes, ointment, suspension or solution prepared according to conventional pharmaceutical practices.

These compounds of formula(I) can be administered at a dosage of from about 1 mg/kg to about 1000 mg/kg of body weight per day. The preferred dosage range is from about 5 mg/kg to about 200 mg/kg of body weight per day.

The compounds of the present invention have extremely low toxicity. The $LD_{50}$ in mice is in excess of 5000 mg/kg of body weight.

The present invention is further illustrated by the following detailed examples.

EXAMPLE 1

(1) In a mixture of 50 ml of dry dimethylsulfoxide and 100 ml of dry tetrahydrofuran were dissolved 30 g of O,N-dibenzyloxycarbonyl-des-N-methylerythromycin A and 18 ml of methyl iodide.

The solution was stirred under cooling at $-12°--10°$ C. in a nitrogen stream and 2.4 g of 55-65% sodium hydride oily dispersion were added thereto in small portions. The mixture was stirred for a further one hour. After completion of the reaction, 50 ml of triethylamine were poured into the reaction mixture with stirring under ice-cooling, and the precipitates were filtered off. The obtained solid product was washed thoroughly with ethyl acetate, and the washings and the mother liquor were combined. The combined liquor was washed with a saturated aqueous sodium chloride solution and dried over anhydrous magnesium sulfate. The solvent was evaporated in vacuo and the crude product was applied onto a silica gel dry column (E. Merck Darmstadt; silica gel 60 for column chromatography, 70-230 mesh, $\phi 5.4 \times 60$ cm), and eluted with a mixture of ethyl acetate and n-hexane (1:1).

15 ml each of fraction was collected and analyzed by silica gel thin layer chromatography (E. Merk Darmstadt; precoated thin layer chromatography plate silica gel 60 F254) for the presence of the reaction product, developing in a mixture of ethyl acetate and n-hexane (1:1). The fractions having Rf value 0.16 were combined (c.f., Rf value of starting compound 0.07) and the solvent was evaporated in vacuo, affording 12.2 g of a colorless froth.

(2) In a mixture of 1.32 g of sodium acetate, 0.8 ml of acetic acid, 40 ml of water and 200 ml of ethanol were dissolved 10 g of the colorless froth obtained in item(1), and 1.0 g of palladium black was added to the above solution. Catalytic reduction was performed for 5 hours at room temperature under atmospheric pressure in a gentle hydrogen stream. 32 ml of 37% aqueous formaldehyde solution were poured into the reaction mixture and the catalytic reduction was continued for a further 7 hours. After completion of the reaction, the catalyst was filtered off and the filtrate was concentrated under reduced pressure approximately to a quarter volume. To the concentrate were added 100 ml of water, and the mixture was adjusted to about pH 10 with an aqueous sodium carbonate solution. The mixture was extracted thoroughly with chloroform and the extract was washed with water and dried. After evaporation of the solvent in vacuo, the residue was recrystallized from a mixture of chloroform and diethyl ether, giving 6 g of crystals.

The crystals were stirred for 5 hours in 500 ml of diethyl ether and filtered off. The filtrate was concentrated to dryness and the residual substance was recrystallized from a mixture of chloroform and diethyl ether, giving 4.5 g of 6-O-methylerythromycin A in the form of colorless needles.

(3) A chloroform solution of 1 g of the crystals obtained in item(2) was absorbed on 5 g of a reversed phase silica gel (E. Merck Darmstadt, silica gel 60 silanized for column chromatography, 70-230 mesh) and the solvent was evaporated under reduced pressure. The silica gel was placed on a column packed with the reversed phase silica gel ($\phi 5.0 \times 40$ cm), and eluted with a mixture of methanol and a 0.1 M phosphate buffer solution (pH 7.0) (3:2) to collect each 15 ml of eluate.

Each fraction was analyzed by thin layer chromatography (E. Merck Darmstadt. thin layer chromatography plate silica gel 60 silanized precoated, thickness 0.25 mm), developing in a mixture of methanol and a 0.1 M phosphate buffer solution (pH 7.0) (3:2). The fractions having Rf value 0.42 (c.f., erythromycin A, Rf value 0.46) were combined and most of the methanol was evaporated in vacuo. The residue was made alkaline with sodium carbonate and extracted with chloroform. The chloroform layer was washed with water, dried and concentrated in vacuo. The crystals obtained were recrystallized from a mixture of chloroform and diisopropyl ether (1:2), giving 700 mg of pure 6-O-methylerythromycin A (formula(I), $R^1$ is hydrogen) in the form of colorless needles.

m.p. 217°-220° C. (with decomposition).

Elementary analysis for $C_{38}H_{69}NO_{13}$; Calcd. (%); C: 61.02; H: 9.30; N: 1.87, Found (%): C: 60.37; H: 9.18; N: 1.71.

Mass spectrum m/e: $M^+ = 747$.

$IR\nu_{max}^{CHCl_3}$ cm$^{-1}$ = 3500, 1730, 1690.

$^1$H-NMR (CDCl$_3$): $\delta$ = 0.84 (dd, 3H), 1.40 (s, 3H), 2.28 (s, 6H), 3.03 (s, 3H), 3.33 (s, 3H), 4.44 (d, 1H), 4.93 (dd, 1H), 5.06 (dd, 1H).

$UV\lambda_{max}^{CHCl_3}$ nm ($\epsilon$): 288 (27.9).

EXAMPLE 2

(1) In 150 ml of dry N,N-dimethylformamide were dissolved 39.6 g of O,N-dibenzyloxycarbonyl-des-N-methylerythromycin A and 17 ml of methyl iodide. To the solution were added with stirring, 2.3 g of 50-55% sodium hydride oily dispersion, in small portions, under cooling at 0°-5° C. in a nitrogen stream. The mixture was stirred for a further one hour.

After completion of the reaction, 50 ml of triethylamine were poured into the reaction mixture, under ice-cooling, and the resulting precipitates were filtered off. The solid substance thus obtained was washed thoroughly with ethyl acetate and the washings were combined with the mother liquor. The combined solution was washed with a saturated aqueous sodium chloride solution and dried over anhydrous magnesium sulfate. The solvent was evaporated in vacuo and the resulting product was purified by silica gel column chromatography and detected by thin layer chromatography (E. Merck Darmstadt, precoated thin layer chromatography plate silica gel 60 F254), developing in a mixture of ethyl acetate and n-hexane (2:1). The fractions having Rf value 0.33 (c.f., Rf value of starting compound 0.20) were combined and the solvent was evaporated in vacuo, giving 10 g of 6,11-di-O-methyl-O,N-dibenzyloxycarbonyl-des-N-methylerythromycin A in the form of colorless needles.

m.p. 108°-110° C.

NMR (CDCl$_3$): $\delta$ = 2.81 and 2.85 (3H), 3.07 (s, 3H), 3.57 (s, 3H), 5.07-5.28 (4H), 7.32-7.50 (10H).

(2) In a mixture of 0.4 ml of acetic acid, 20 ml of water and 100 ml of ethanol were dissolved 1.8 g of 6,11-di-O-methyl-O,N-dibenzyloxycarbonyl-des-N-methylerythromycin A and 0.66 g of sodium acetate, and catalytic reduction was performed at room temperature under atmospheric pressure in a gentle hydrogen stream, by using 0.2 g of palladium black. After completion of the reaction, the catalyst was filtered off, and the filtrate was concentrated under reduced pressure approximately to a quarter volume. 50 ml of water were added to the concentrate and the mixture was adjusted to about pH 10 with an aqueous sodium carbonate solution, then extracted with chloroform. The chloroform layer was washed with water, dried over anhydrous magnesium sulfate, and the solvent was evaporated in vacuo. The residue was recrystallized from a mixture of chloroform and ethyl ether, affording 0.93 g of 6,11-di-O-methyl-des-N-methylerythromycin A in the form of colorless needles.

m.p. 224.5°-227° C.

NMR (CDCl$_3$): δ=2.42 (s, 3H), 3.10 (s, 3H), 3.32 (s, 3H), 3.57 (s, 3H).

(3) To 50 ml of methanol were added 0.4 g of 6,11-di-O-methyl-des-N-methylerythromycin A and 1 ml of 37% aquous formaldehyde solution.

After the mixture was allowed to stand for one hour at room temperature, catalytic reduction was performed at room temperature under atmospheric pressure in a gentle hydrogen stream, by using 0.2 g of 5% palladium on charcoal. After completion of the reaction, the catalyst was filtered off and most of the methanol was evaporated from the filtrate in vacuo. 50 ml of water were added to the residue and the mixture was made alkaline by addition of sodium carbonate. The mixture was extracted with dichloromethane and the extract was washed with water and dried. The solvent was evaporated in vacuo and the residue was recrystallized from a mixture of chloroform and diethyl ether, giving 0.4 g of 6,11-di-O-methyl-erythromycin A (formula(I), $R^1$ is methyl) in the form of colorless needles.

m.p. 251°-253° C. (with decomposition).

Elementary analysis for $C_{39}H_{71}NO_{13}$: Calcd. (%): C: 61.47; H: 9.39; H: 1.84, Found (%): C: 61.48; H: 9.29; H: 1.72.

Mass spectrum: $M^+ = 761$.

IR$\nu_{max}^{CHCl_3}$ cm$^{-1}$ = 3500, 1720, 1705.

NMR (CDCl$_3$): δ=1.42 (s, 3H), 2.33 (s, 6H), 3.12 (s, 3H), 3.35 (s, 3H), 3.60 (s, 3H).

UV$\lambda_{max}^{CHCl_3}$ nm (ε): 292 (23.6).

EXAMPLE 3

In a mixture of 0.8 ml of acetic acid, 40 ml of water and 200 ml of ethanol were dissolved 9.4 g of 6,11-di-O-methyl-O,N-dibenzyloxycarbonyl-des-N-methylerythromycin A and 1.32 g of sodium acetate. Catalytic reduction was performed for 5 hours at room temperature under atmospheric pressure, by using 1 g of palladium black. Into the reaction mixture were poured 32 ml of 37% aqueous formaldehyde solution and catalytic reduction was continued for a further 7 hours. After completion of the reaction, the catalyst was filtered off and the filtrate was concentrated in vacuo approximately to a quarter volume. 100 ml of water were added to the concentrate and the mixture was adjusted to about pH 10 with an aqueous sodium carbonate solution. The mixture was extracted with chloroform and the extract was washed and dried. The solvent was evaporated in vacuo and the residue was recrystallized from a mixture of dichloromethane and petroleum ether, affording 6 g of 6,11-di-O-methylerythromycin A (formula(I), $R^1$ is methyl) in the form of colorless needles.

The physicochemical properties of the compound coincided with those of the compound obtained in Example 2(3).

Experiments made on pharmaceutical properties of the compounds of the present invention are summarized below. In these experiments, "TE-031" and "TE-032" refer to 6-O-methylerythromycin A and 6,11-di-O-methylerythromycin A of the present invention, respectively.

EXPERIMENT 1

Acid stability

The compound of the formula(I) was treated in the Clark-Lubs's buffer solution at pH 2 for the prescribed period of time.

Thereafter, the remaining antibacterial activity was determined by a disc method, using *Staphylococcus aureus* FDA 209P. Erthromycin A was also tested for the control. The results are shown in Table 1.

TABLE 1

| | Acid stability | | | | |
|---|---|---|---|---|---|
| | Time$_{(min.)}$ | | | | |
| | Remaining activity (%) | | | | |
| Compound | 0 | 15 | 30 | 60 | 120 |
| TE-031 | 100 | 100 | 95 | 80 | 65 |
| TE-032 | 100 | 100 | 95 | 85 | 65 |
| Erythromycin A | 100 | 1.5 | 0.5 | 0 | 0 |

EXPERIMENT 2

Antibacterial activity

The compound of the formula(I) was tested for the antibacterial activity by the agar plate dilution method, using erythromycin A for the control. The results, indicated as the minimum inhibitory concentrations (MIC), are shown in Table 2.

TABLE 2

| | Antibacterial spectrum MIC value (mcg/ml) | | |
|---|---|---|---|
| | Compound | | |
| Microorganism | TE-031 | TE-032 | Erythromycin A |
| *Staphylococcus aureus* FDA 209P | 0.05 | 0.1 | 0.2 |
| *Staphylococcus aureus* Smith | 0.2 | 0.1 | 0.4 |
| *Staphylococcus aureus* Terashima | 0.2 | 0.4 | 0.4 |
| *Staphylococcus aureus* TPR-5 | 0.2 | 0.4 | 0.4 |
| **Staphylococcus aureus* TPR-7 | 0.2 | 0.4 | 0.4 |
| ***Staphylococcus epidermidis* TPR-14 | 0.2 | 0.4 | 0.4 |
| *Staphylococcus epidermidis* IID866 | 0.2 | 0.4 | 0.4 |
| *Micrococcus luteus* ATCC 9341 | ≦0.05 | ≦0.05 | ≦0.05 |
| *Bacillus subtilis* ATCC 6633 | 0.05 | 0.05 | 0.1 |
| *Bacillus cereus* ATCC 9634 | 0.2 | 0.4 | 0.4 |
| *Streptococcus faecalis* ATCC 8043 | 0.05 | 0.05 | 0.05 |

*Strain resistant to sulfonamides and penicillins
**Strain resistant to sulfonamides and tetracyclines
***Strain resistant to sulfonamides, penicillins and chloramphenicol

EXPERIMENT 3

In vivo activity

Male ddY mice (body weight, 18–22 g; 14 mice per group) were inoculated with *Staphylococcus aureus* Smith No. 4. The compound of the formula(I) was administered orally one hour after the inoculation, and the number of mice surviving for seven days after the administration was noted. The results are shown in Table 3.

TABLE 3

In vivo activity

| Dose (mg/kg) | The number of surviving mice Compound | | |
|---|---|---|---|
| | TE-031 | TE-032 | Erythromycin A |
| 400 | 14 | 14 | 14 |
| 100 | 14 | 14 | 11 |
| 25 | 13 | 7 | 1 |
| 6.25 | 3 | 4 | 0 |
| 1.56 | 1 | 0 | 0 |
| 0.40 | 0 | 0 | 0 |

What is claimed is:

1. An erythromycin compound of the formula

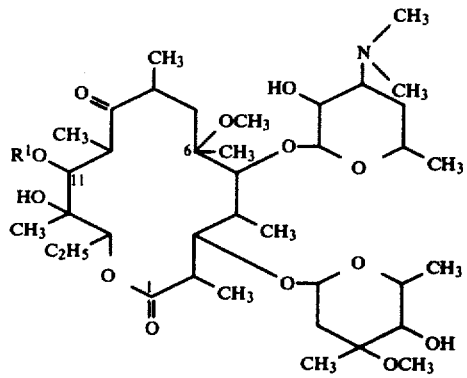

wherein $R^1$ is hydrogen or methyl, and a pharmaceutically acceptable salt thereof.

2. A compound according to claim 1 wherein $R^1$ is hydrogen.

3. A compound according to claim 1 wherein $R^1$ is methyl.

* * * * *

UNITED STATES PATENT AND TRADEMARK OFFICE

CERTIFICATE EXTENDING PATENT TERM
UNDER 35 U.S.C. § 156

PATENT NO.:     4,331,803

DATED:          May 25, 1982

INVENTORS:      Yoshiaki Watanabe et al.

PATENT OWNER:   Taisho Pharmaceutical Co., Ltd.

This is to certify that there has been presented to the

COMMISSIONER OF PATENTS AND TRADEMARKS an application under 35 U.S.C. § 156 for an extension of the patent term. Since it appears that the requirements of the law have been met, this certificate extends the term of the patent for the period of 1,465 DAYS with all rights pertaining thereto as provided by 35 U.S.C. § 156(b).

I have caused the seal of the Patent and Trademark Office to be affixed this 20th day of May 1993.

Michael K. Kirk
Acting Commissioner of Patents and Trademarks